US008861821B2

(12) United States Patent
Osumi

(10) Patent No.: US 8,861,821 B2
(45) Date of Patent: Oct. 14, 2014

(54) ULTRASOUND DIAGNOSIS APPARATUS

(75) Inventor: Ryota Osumi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 795 days.

(21) Appl. No.: 12/765,386

(22) Filed: Apr. 22, 2010

(65) Prior Publication Data

US 2010/0286525 A1 Nov. 11, 2010

(30) Foreign Application Priority Data

May 8, 2009 (JP) ................. 2009-113667

(51) Int. Cl.
| | |
|---|---|
| *G06K 9/00* | (2006.01) |
| *G01S 7/52* | (2006.01) |
| *G06T 5/10* | (2006.01) |
| *G06T 5/00* | (2006.01) |
| *A61B 8/14* | (2006.01) |

(52) U.S. Cl.
CPC ............. *A61B 8/14* (2013.01); *G01S 7/52077* (2013.01); *G06T 5/10* (2013.01); *G06T 2207/20064* (2013.01); *G06T 2207/10132* (2013.01); *G06T 2207/20192* (2013.01); *G06T 2207/10076* (2013.01); *G06T 2207/30004* (2013.01); *G06T 2207/10136* (2013.01); *G06T 5/002* (2013.01); *G06T 2207/20016* (2013.01); *G06T 2207/10072* (2013.01); *G06T 2207/20182* (2013.01)
USPC ........................................... 382/131

(58) Field of Classification Search
CPC .................................... G06T 7/0012
USPC ......................................... 382/131
See application file for complete search history.

(56) References Cited

U.S. PATENT DOCUMENTS 5,976,088 A * 11/1999 Urbano et al. ............... 600/443
(Continued)

FOREIGN PATENT DOCUMENTS

| JP | 11-311618 A | 11/1999 |
|---|---|---|
| JP | 2005-81154 A | 3/2005 |
| JP | 2005-296331 A | 10/2005 |

(Continued)

OTHER PUBLICATIONS

Japanese Office Action Issued Jun. 18, 2013 in Patent Application No. 2009-113667.

*Primary Examiner* — Sheetal R Rangrej
(74) *Attorney, Agent, or Firm* — Oblon, Spivak, McClelland, Maier & Neustadt, L.L.P.

(57) ABSTRACT

An ultrasound diagnosis apparatus of the present invention has: an image generator configured to execute transmission/reception of ultrasound waves to chronologically generate ultrasound image data of plural frames; a multiresolution decomposition part configured to hierarchically perform multiresolution decomposition on the ultrasound image data to acquire first-order to $n^{th}$-order (n represents a natural number of 2 or more) low-band decomposition image data and first-order to $n^{th}$-order high-band decomposition image data; a feature amount calculator configured to calculate a feature amount based on the acquired low-band decomposition image data; a filtering processor configured to perform a filtering operation on the calculated feature amount; and a multiresolution composition part configured to execute multiresolution composition using the low-band decomposition image data and high-band decomposition image data to generate a composite image. Thus, the apparatus can efficiently reduce change in speckle/noise in the temporal direction and perform a process without a time phase delay.

8 Claims, 9 Drawing Sheets

(56) References Cited

U.S. PATENT DOCUMENTS

| | | | |
|---|---|---|---|
| 6,912,319 B1* | 6/2005 | Barnes et al. | 382/240 |
| 7,236,637 B2* | 6/2007 | Sirohey et al. | 382/240 |
| 2006/0084869 A1* | 4/2006 | Kim et al. | 600/437 |
| 2011/0268328 A1* | 11/2011 | Bar-Aviv et al. | 382/128 |

FOREIGN PATENT DOCUMENTS

| | | | |
|---|---|---|---|
| JP | 2006-116307 | | 5/2006 |
| JP | 2009-82469 A | | 4/2009 |
| WO | WO 99/46731 | * | 9/1999 |
| WO | WO 2007/001236 | * | 1/2007 |

* cited by examiner

FIG. 4

| | x-DIRECTION | y-DIRECTION | t-DIRECTION |
|---|---|---|---|
| 301 | L | L | L |
| 302 | H | L | L |
| 303 | L | H | L |
| 304 | H | H | L |
| 305 | L | L | H |
| 306 | H | L | H |
| 307 | L | H | H |
| 308 | H | H | H |

L: LOW-PASS
H: HIGH-PASS

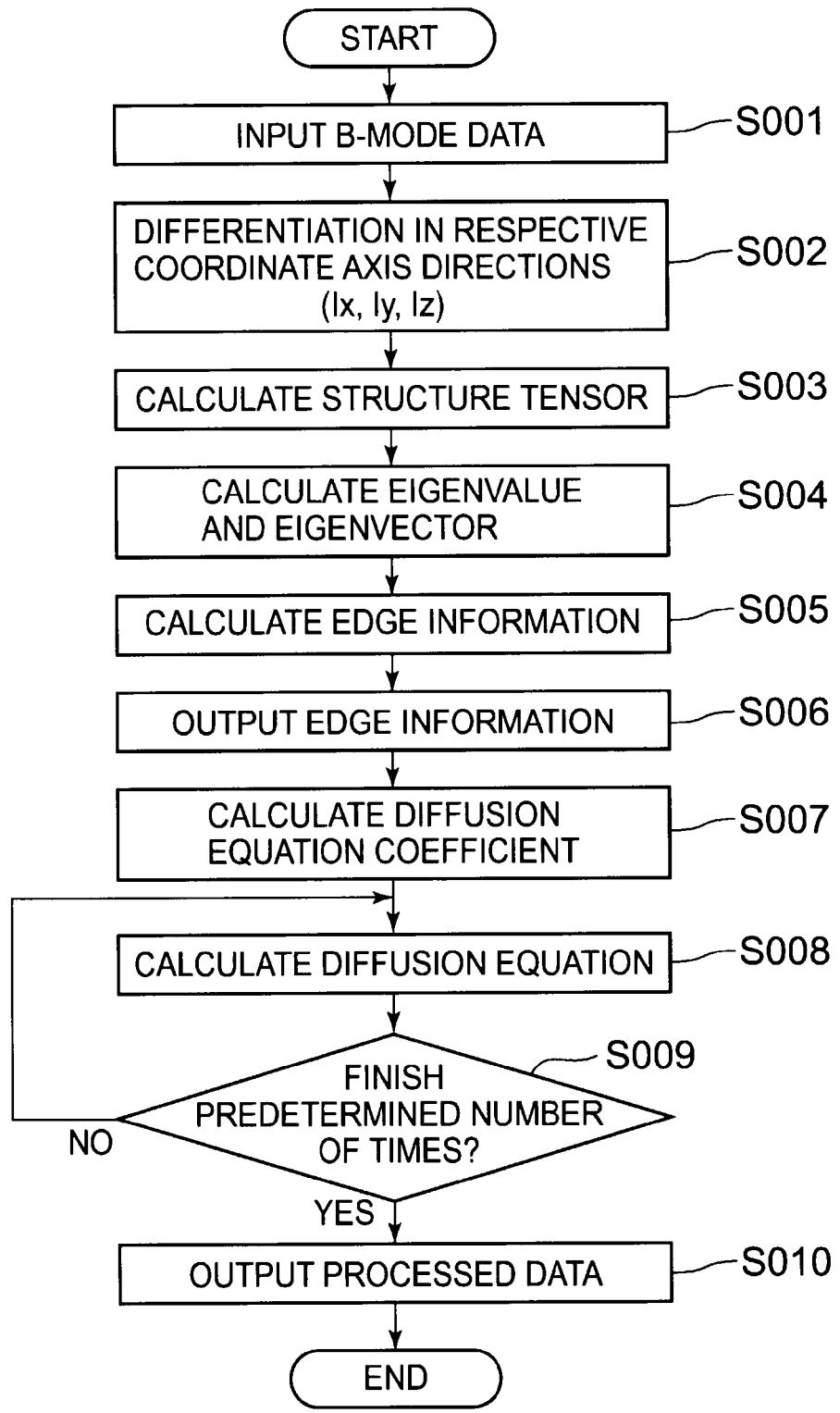

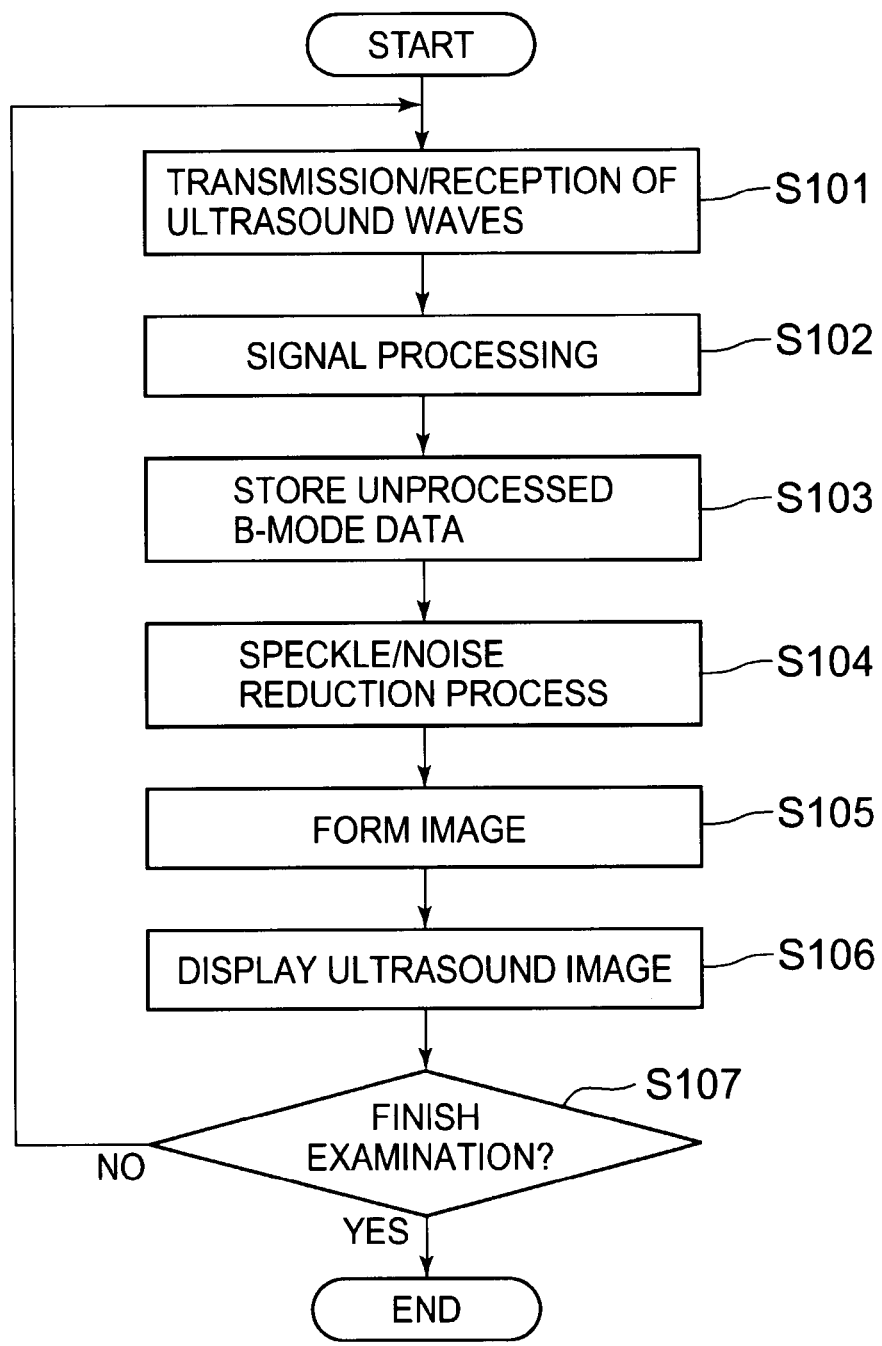

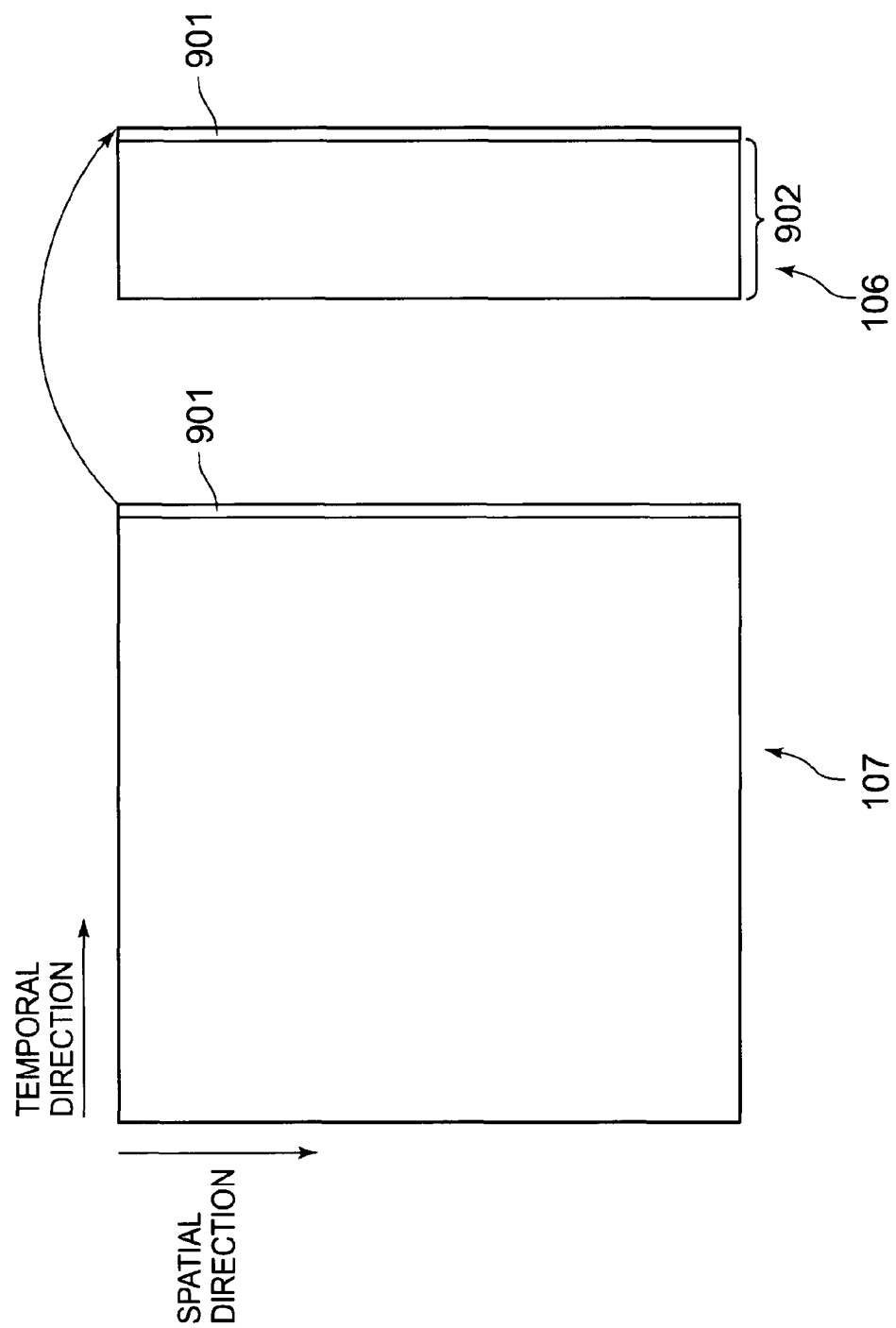

ULTRASOUND DIAGNOSIS APPARATUS

BACKGROUND OF THE INVENTION

1. Field of the Invention

The present invention relates to an ultrasound diagnosis apparatus that transmits ultrasound waves to a subject and obtains an ultrasound image based on the waves reflected from the subject.

More specifically, the present invention relates to an ultrasound diagnosis apparatus that executes a correction process on a generated ultrasound image.

2. Description of the Related Art

An ultrasound diagnosis apparatus transmits, to a subject, ultrasound waves generated from transducers incorporated in an ultrasound probe. The ultrasound diagnosis apparatus receives, by the transducers, reflected waves from a subject tissue of the transmitted ultrasound waves, generates an ultrasound tomographic image of the subject from the received reflected waves, and displays the ultrasound tomographic image.

Signals received from a plurality of subject tissues adjacent to each other interfere with each other because having different phases.

This interference makes a vision different from when only amplitudes are composed, and generates a speckled image pattern. Such an image pattern is called speckle. This speckle prevents accurate observation of the position and shape of the boundary of the subject tissues.

The accurate observation is also prevented by occurrence of noise. Such speckle and noise occur not only in the spatial direction but also in the temporal direction.

Up to now, various processing methods for reducing speckle and noise have been proposed.

For example, a technique of using a temporal-direction IIR (Infinite Impulse Response) filter has been proposed. This technique is a technique of using a filter that, assuming an image acquired at time t is represented by I(t) and an image having been processed by the filter is represented by $J_t$, satisfies a relation of $J_t=(1-a)I_t+aJ_{t-1}$, wherein a is 1 or less. This technique enables reduction of speckle and noise that vary with time.

However, this technique reduces noise by adding the proportion of a of the past data $J_{t-1}$ to the proportion of (1−a) of the present data $I_t$.

Therefore, for a strenuously moving tissue such as the diaphragm and the heart, there is a problem that, in a superimposed image, each image of the strenuously moving tissue remains like an afterimage and blur or the like occurs.

In a case that an image is generated for each frame, which is the unit of a set of data necessary for generating one tomographic image, a motion vector of each image (image of an organ, for example) in a past frame is detected from the image.

Then, the position of an image in a next frame is predicted by using the motion vector, and a filter process or the like is performed at the predicted position.

With this technique, it is possible to perform image processing including displacement of an image with time.

However, as mentioned above, the process of detecting the motion vector is required in addition to the noise reduction process.

Therefore, there is a problem that the process gets slow.

Further, in order to define a tissue part, a speckle/noise reduction filter has been used conventionally.

As the speckle/noise reduction filter, a filter using a directional feature amount in a two-dimensional or three-dimensional space is used.

The directional feature amount is the size or direction of an edge. The edge is a part in which the luminance largely changes, such as the outside of a tissue. Also, the edge is a part other than noise.

As the abovementioned filter using the directional feature amount, it is possible to use a filter that blurs an image in the edge direction, or a filter that emphasizes the contrast of an image in a direction orthogonal to the edge direction. As the filter that blurs an image in the edge direction, it is possible to use, for example, a filter that obtains an average value of a row of points.

Further, as the filter that emphasizes the contrast in the direction orthogonal to the edge direction, it is possible to use, for example, a filter that, by a threshold, decreases the luminance outside the edge while increases the luminance inside the edge.

Use of the filter that blurs an image in the edge direction makes it possible to obtain an image with smooth shading in the edge direction.

Further, use of the filter that emphasizes the contrast of an image in the direction orthogonal to the edge direction makes it possible to obtain an image with an edge defined and a tissue part emphasized.

As a method for obtaining the abovementioned directional feature amount, a technique of using multiresolution decomposition is proposed.

Multiresolution decomposition is a method of decomposing arbitrary video signals into a plurality of videos having different frequency bands (spatial frequency bands).

As multiresolution decomposition, it is possible to use wavelet transform. This wavelet transform is decomposition into a video of low-frequency components and a video of high-frequency components that have a $2^{-1}$ size of an inputted video.

Based on videos obtained by the wavelet transform, the edge of an image of low-band spatial frequency is detected by using a diffusion filter, and the direction of the edge is obtained for each pixel.

A technique of smoothing pixels by using the filter that blurs an image in the tangent direction of the edge while sharpening pixels by using the filter that emphasizes the contrast in the normal direction of the edge is proposed (refer to, for example, Japanese Unexamined Patent Application Publication JP-A 2006-116307).

This enables definition of a tissue part in the video of low-frequency components.

In the image processing by multiresolution decomposition and the respective filters described in JP-A 2006-116307, a noise reduction process is performed with respect to the spatial direction.

However, in the technique described in JP-A 2006-116307, the image processing by multiresolution decomposition and the respective filters is not executed on an image including the temporal direction.

Therefore, such a method of performing the noise reduction process with respect to only the spatial direction may cause noise and speckle in an image with respect to the temporal direction.

Further, in a case that the filtering process with respect to the space is applied as it is, there is a problem that a time-phase delay occurs and an image immediately after generated (a real-time image) cannot be displayed.

SUMMARY OF THE INVENTION

The present invention uses a noise reduction process with a directional feature amount performed in the spatial direction, with respect to coordinates including the temporal direction (space+time).

To be specific, an object of the present invention is to provide a technique of, by using a process without occurrence of a time phase delay, reducing noise and speckle in the temporal direction and emphasizing a tissue part in an ultrasound image of a strenuous tissue.

In a first aspect of the present invention, an ultrasound diagnosis apparatus comprises: an image generator configured to execute transmission and reception of ultrasound waves to chronologically generate ultrasound image data of plural frames; a multiresolution decomposition part configured to hierarchically execute multiresolution decomposition on the ultrasound image data to obtain first-order to $n^{th}$-order (n represents a natural number of 2 or more) low-band decomposition image data and first-order to $n^{th}$-order high-band decomposition image data; a feature amount calculator configured to calculate a feature amount based on the obtained low-band decomposition image data; a filtering processor configured to execute a filter operation on the calculated feature amount; and a multiresolution composition part configured to execute multiresolution composition by using the low-band decomposition image data and the high-band decomposition image data to generate a composite image.

In a second aspect of the present invention, an ultrasound diagnosis apparatus comprises: an image generator configured to execute transmission and reception of ultrasound waves to chronologically generate ultrasound image data of plural frames; a multiresolution decomposition part configured to hierarchically execute multiresolution decomposition on the ultrasound image data to obtain first-order to $n^{th}$-order (n represents a natural number of 2 or more) low-band decomposition image data and first-order to $n^{th}$-order high-band decomposition image data; a multiresolution composition part configured to perform multiresolution composition by using the low-band decomposition image data and the high-band decomposition image data to generate a composite image; a feature amount calculator configured to calculate a feature amount based on the obtained low-band decomposition image data; a filtering processor configured to perform a filter operation on the calculated feature amount; and a high-band-level controller configured to weight the first-order to $n^{th}$-order high-band decomposition image data obtained from the multiresolution decomposition part, by a feature amount of each corresponding order.

BRIEF DESCRIPTION OF THE DRAWINGS

FIG. 4 is a view showing a usage pattern of a filter used in the respective coordinate axis directions in three-dimensional wavelet transform including the temporal axis.

FIG. 6 is a flow chart showing the procedure of a filtering process by a nonlinear anisotropic diffusion filter in the third-order hierarchy.

FIG. 7 is a flow chart of a general operation of an ultrasound diagnosis apparatus according to a first embodiment.

FIG. 9 is a view for explaining accumulation of B-mode data and a speckle/noise reduction process using the accumulated B-mode data in a modification 1.

DETAILED DESCRIPTION OF THE EMBODIMENTS

First Embodiment

An ultrasound diagnosis apparatus according to a first embodiment of the present invention will be described below.

Figure 1:
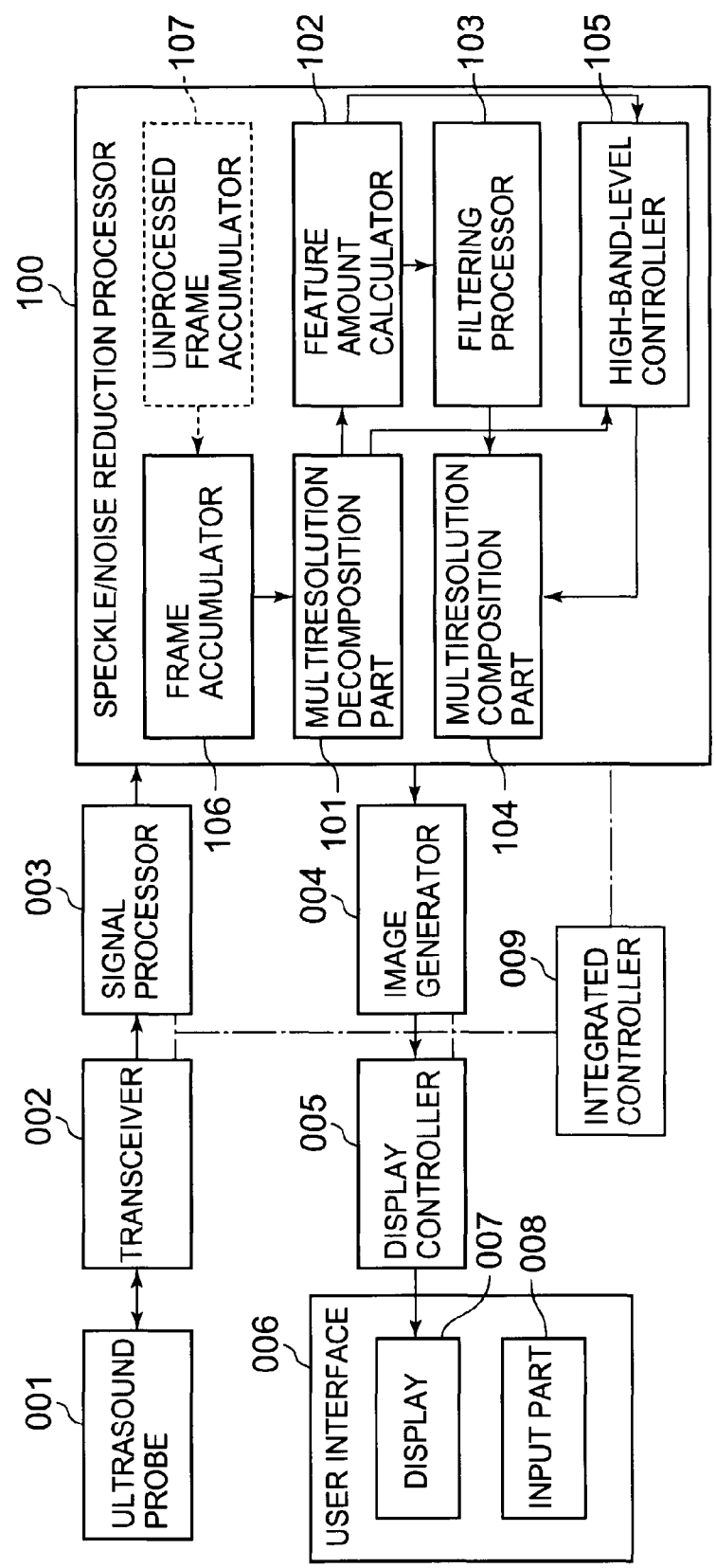
FIG. 1 is a block diagram showing the configuration of an ultrasound diagnosis apparatus according to the present invention.

FIG. 1 is a block diagram showing the function of the ultrasound diagnosis apparatus according to this embodiment.

As shown in FIG. 1, the ultrasound diagnosis apparatus according to this embodiment has an ultrasound probe 001, a transceiver 002, a signal processor 003, an image generator 004, a speckle/noise reduction processor 100, a display controller 005, and a user interface 006. The user interface 006 has a display 007 such as a monitor, and an input part 008 such as a keyboard and a mouse.

The ultrasound probe 001 has a plurality of piezoelectric transducers. The ultrasound probe 001 converts pulse signals into ultrasound waves by using the piezoelectric transducers, and transmits the ultrasound waves obtained by the conversion to a subject. The pulse signals are inputted from the transceiver 002 described later.

Further, the ultrasound probe 001 receives, by piezoelectric elements, the ultrasound waves reflected by the subject (ultrasound echoes). Then, the ultrasound echoes are converted into electric signals (referred to as "echo signals" hereinafter) and outputted to the transceiver 002. A set of ultrasound echoes obtained by one time of transmission/reception of ultrasound waves between the respective transducers and the subject is called one frame. That is to say, one ultrasound image is generated from one frame. The number of frame scans per unit time is called a frame rate. In this embodiment, the ultrasound probe 001 repeatedly scans the same region (scan position) of the subject at a predetermined frame rate.

In order to make the ultrasound waves transmitted from the ultrasound probe 001 converge into a beam, the transceiver 002 delays arrival of the pulse signals at the respective piezoelectric transducers of the ultrasound probe 001. That is to say, the transceiver 002 makes the time of arrival of the pulse signals later at the piezoelectric transducers closer to the center of the ultrasound probe 001. By delaying arrival of the pulse signals at the respective piezoelectric transducers, the timing for driving the respective piezoelectric transducers is delayed, and the generated ultrasound waves are made to converge into a beam.

In reception of the ultrasound echoes, the echo signals of the respective transducers, which are analog signals, are amplified by the transceiver 002, and delayed a desired delay time by a reception delay circuit or the like (not shown). Then, after executing A/D conversion on the echo signals, the transceiver 002 performs an addition process based on the converted signals. Then, the transceiver 002 outputs the signals after the addition process, to the signal processor 003.

The signal processor 003 has a B-mode process unit and a Doppler process unit. The signal processor 003 receives the signals from the transceiver 002.

The B-mode process unit receives the signals from the transceiver 002. Then, the B-mode process unit executes logarithmic compression, envelop detection or the like, on the received signals.

Besides, the B-mode process unit generates B-mode data that expresses luminance by the intensity of the signals.

The Doppler process unit performs frequency analysis of speed information based on the signals from the transceiver 002. Then, the Doppler process unit extracts the echo components of a blood flow, tissue and contrast agent due to the Doppler Effect to generate Doppler data of blood-flow information such as the average speed, dispersion and power.

The signal processor 003 outputs the B-mode data generated by the B-mode process unit and the Doppler data generated by the Doppler process unit (both the data will be referred to as "raw data" hereinafter) to the speckle/noise reduction processor 100.

The ultrasound probe 001, the transceiver 002, and the signal processor 003 are equivalent to the "image generator" in the present invention.

Into the speckle/noise reduction processor 100, the raw data are inputted from the signal processor 003. Then, the speckle/noise reduction processor 100 executes a process for reducing speckle and noise on the inputted raw data. This speckle/noise reduction process will be described in detail later. Then, the speckle/noise reduction processor 100 outputs the raw data after the speckle/noise reduction process to the image generator 004.

The image generator 004 has a DSC (Digital Scan Converter).

Into the image generator 004, the raw data after the speckle/noise reduction process by the speckle/noise reduction processor 100 is inputted.

The DSC converts the inputted raw data from a coordinate system corresponding to scan lines of ultrasound scan to a coordinate system for displaying on the monitor or the like.

The image generator 004 has a storing region such as a memory.

Into the storing region of the image generator 004, the image data generated by the DSC are sequentially stored. The stored image data are retrieved with the user interface 006 by an operator such as a doctor and a medical technologist (simply referred to as the "operator" hereinafter). The retrieved image data are displayed on the display 007.

The image generator 004 outputs the generated image data to the display controller 005.

The display controller 005 receives input of the image data from the image generator 004. Then, the display controller 005 controls the display 007 to display ultrasound images such as a B-mode image and a Doppler image based on the inputted image data. Hereinafter, the B-mode image and the Doppler image will be simply referred to as the "ultrasound image" when not distinguished from each other.

The image generator 004 and the display controller 005 having the abovementioned functions are equivalent to the "display controller" of the present invention.

An integrated controller 009 performs control of the timing of operations of the respective function parts and control of the passing of data between the respective function parts. A dashed-dotted line in FIG. 1 shows the flow of a control command.

(Speckle/Noise Reduction Process)

Next, the speckle/noise reduction process executed by the speckle/noise reduction processor 100 will be described. The speckle/noise reduction processor 100 is capable of executing the process of reducing speckle and noise on both B-mode data and Doppler data. Therefore, in the following description, the process of reducing speckle and noise on B-mode data will be taken for an example.

Further, in the following description, in order to facilitate the description, the speckle/noise reduction process will be described based on two-dimensional ultrasound image data.

The speckle/noise reduction process can also be performed for a three-dimensional image. The three-dimensional ultrasound image is four-dimensional when the temporal dimension is included. For calculation thereof, only one row and one column are added in the matrix calculation described below.

In the following description, data composing one B-mode image will be referred to as B-mode data of one frame.

Further, the number of B-mode data corresponding to the number of B-mode images will be referred to as the number of frames. B-mode data of one frame corresponds to "one ultrasound image data" in the present invention.

Figure 2:
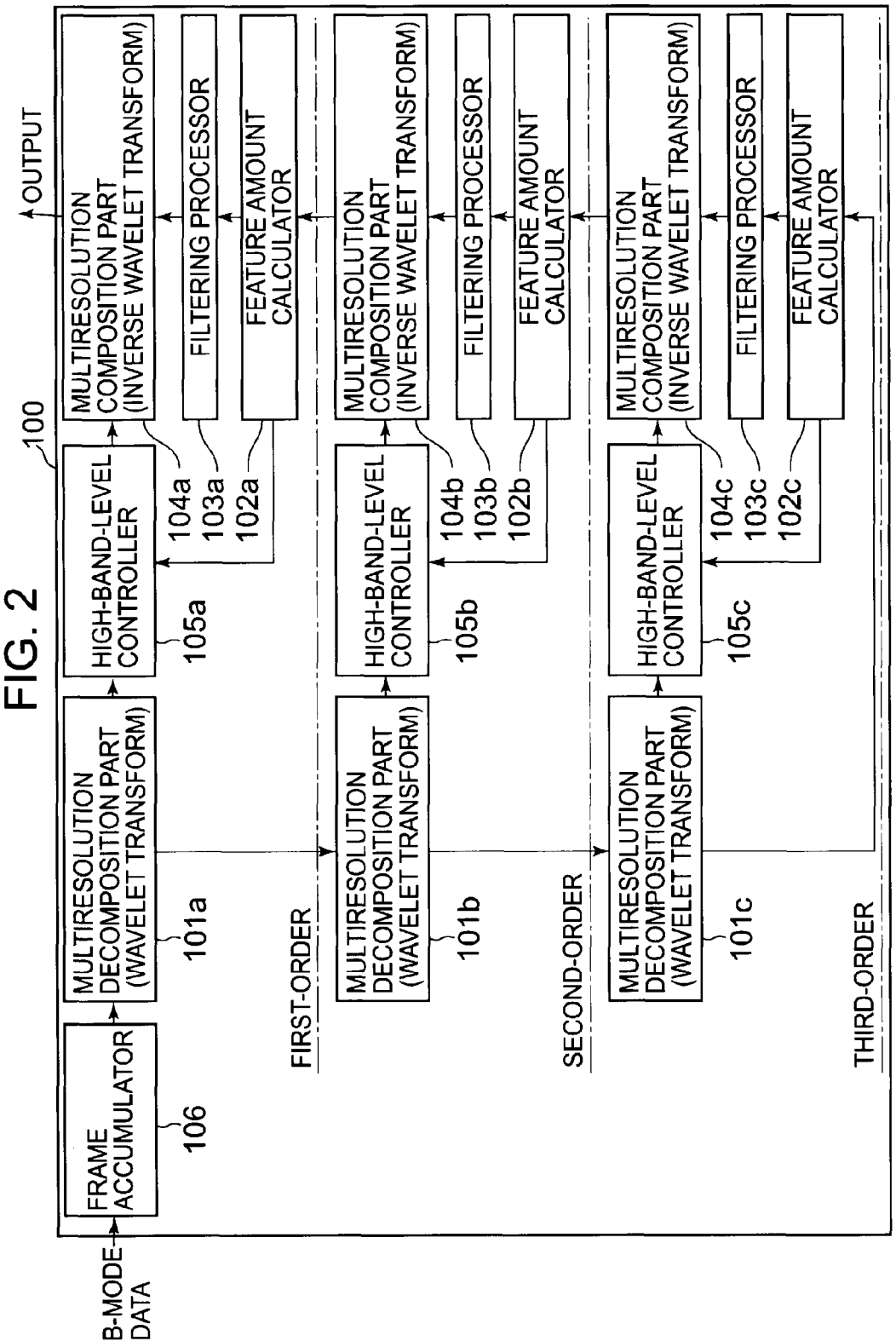
FIG. 2 is a diagram showing a detailed configuration of a speckle/noise reduction processor in the present invention.

FIG. 2 is a diagram showing a detailed configuration of the speckle/noise reduction processor 100. As shown in FIG. 2, in order to perform a process from multiresolution decomposition to multiresolution composition, the speckle-noise reduction processor 100 has a multiple structure composed of a plurality of hierarchies (first-order to third-order) as shown by a dashed-dotted line. In this embodiment, in order to facilitate the description, the highest order in the process from multiresolution decomposition to multiresolution composition will be third-order. The process from multiresolution decomposition to multiresolution composition can be performed in the range from first-order to $n^{th}$-order (n denotes a natural number of 2 or more).

Further, wavelet transform is used as multiresolution decomposition in this embodiment. The wavelet transform is an example of multiresolution decomposition. Alternatively, another multiresolution decomposition method such as the Laplacian Pyramid method or the Gabor transform may be used.

The wavelet transform/inverse transform in this embodiment is so-called discrete wavelet transform/inverse transform. In the following description, a larger order in FIG. 2 (namely, a lower position in FIG. 2) represents a higher hierarchy.

The speckle/noise reduction processor 100, as shown in FIG. 2, is provided with a multiresolution decomposition part 101 (101a, 101b, 101c), a feature amount calculator 102 (102a, 102b, 102c), a filtering processor 103 (103a, 103b, 103c), a multiresolution composition part 104 (104a, 104b, 104c), and a high-band-level controller 105 (105a, 105b, 105c) for each hierarchy.

Further, the speckle/noise reduction processor 100 is provided with a frame accumulator 106.

The frame accumulator 106 has a storing medium such as a hard disk and a memory. The frame accumulator 106 receives input of B-mode data from the signal processor 003. Then, the frame accumulator 106 stores B-mode data of a predetermined number of frames (number of sheets) from a starting frame for acquisition to a latest frame. Since B-mode data are sequentially generated with time, the B-mode data are accumulated into the frame accumulator 106 one after another. The respective B-mode data are data of ultrasound images obtained by scanning the same region in the same subject. The B-mode data of the respective frames are different in scanned time.

When B-mode data of a new frame is inputted, the frame accumulator 106 deletes B-mode data of the oldest frame.

However, a storing method by the frame accumulator 106 may be another method as far as the method allows storage of B-mode data of a necessary number of frames. For example, the method may be a method of storing B-mode data of all frames without deleting B-mode data of old frames.

The frame accumulator 106 is equivalent to the "data accumulator" of the present invention.

As shown in FIG. 2, the frame accumulator 106 outputs the stored B-mode data of the predetermined number of frames, to the multiresolution decomposition part 101. In the following description, a set of B-mode data of a predetermined number of frames will be referred to as set B-mode data.

The multiresolution decomposition part 101 receives input of the B-mode data of the predetermined number of frames (the set B-mode data) from the frame accumulator 106. The multiresolution decomposition part 101 of this embodiment performs multiresolution decomposition with respect to the spatial direction and temporal direction. The spatial direction represents a direction in a region in which the subject is scanned. For example, the spatial direction in a two-dimensional tomographic image represents two-dimensional directions of the x-direction and y-direction. The spatial direction in a three-dimensional tomographic image represents three-dimensional directions of the x-direction, y-direction and z-direction. In this embodiment, because an ultrasound image is a two-dimensional image, the multiresolution decomposition part 101 performs multiresolution decomposition for a three-dimensional coordinate system including the temporal axis (spacetime). The multiresolution decomposition part 101 executes three-dimensional wavelet transform on the inputted set B-mode data. The set B-mode data is decomposed into one kind of low-band decomposition image data and seven kinds of high-band decomposition image data. The multiresolution decomposition part 101 is equivalent to the "multiresolution decomposition part" of the present invention.

Figure 3:
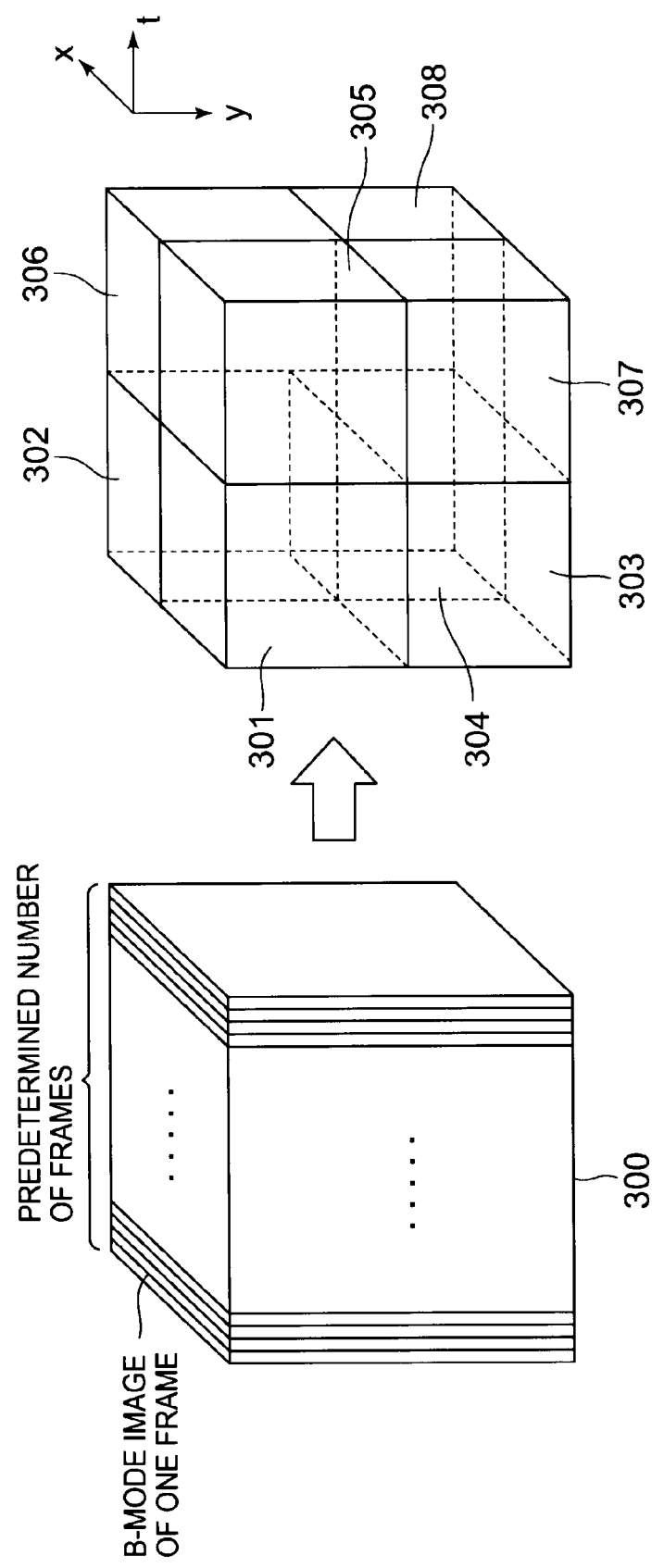
FIG. 3 is a conceptual diagram of multiresolution decomposition by three-dimensional wavelet transform including the temporal axis.

FIG. 3 is a conceptual view of multiresolution decomposition by three-dimensional wavelet transform including the temporal axis.

FIG. 4 is a view showing a pattern of a filter used in the respective coordinate axis directions in three-dimensional wavelet transform including the temporal axis. As shown in FIGS. 3 and 4, the multiresolution decomposition part 101 performs wavelet transform on set B-mode data 300 having spatial dimensions (x, y) and temporal dimension (t) before multiresolution decomposition, by using a one-dimensional low-pass filter (L) and high-pass filter (H) for the respective coordinate axis directions (the respective dimensions) of the xyt orthogonal coordinate axes. Through wavelet transform, the set B-mode data 300 is decomposed into one kind of low-band decomposition image data 301 and seven kinds of high-band decomposition image data 302-308. The low-band decomposition image data 301 includes low-frequency components among frequency components in the set B-mode data 300 before multiresolution decomposition.

Further, the respective high-band decomposition image data 302-308 include high-frequency components in at least one coordinate-axis direction among frequency components included in the set B-mode data 300 before multiresolution decomposition. FIG. 4 shows a usage condition of the low-pass filter or the high-pass filter for each coordinate axis with respect to the low-band decomposition image data 301 and the high-band decomposition image data 302-308 after multiresolution decomposition. In the low-band decomposition image data 301 and high-band decomposition image data 302-308 after multiresolution decomposition, the number of samples for each of the coordinate axes is reduced to half the number of samples for each of the coordinate axes of the set B-mode data 300 before multiresolution decomposition.

The multiresolution decomposition part 101 performs multiresolution decomposition one time, or repeats plural times up to the highest hierarchy. Consequently, as shown in FIG. 2, hierarchies (three hierarchies in this embodiment) are obtained. Each of the hierarchies is expressed by the order. In the case of repeating multiresolution decomposition plural times, the low-band decomposition image data in a next lower hierarchy (a hierarchy shown at a next higher position in FIG. 2) becomes input image data for the next multiresolution decomposition. To be specific, in a case that the multiresolution decomposition part 101 is not one belonging to the highest hierarchy (the third-order hierarchy in this embodiment), the multiresolution decomposition part 101a supplies generated low-band decomposition image data to the multiresolution decomposition part 101b. The multiresolution decomposition part 101b supplies the generated low-band decomposition image data to the multiresolution decomposition part 101c.

Further, the multiresolution decomposition part 101c in the highest hierarchy (third-order hierarchy) supplies the generated low-band decomposition image data to the feature amount calculator 102c in the same hierarchy (third-order hierarchy).

Further, the multiresolution decomposition part 101 in each of the hierarchies supplies the generated high-band decomposition image data to a high-band-level controller 105 in the same hierarchy.

The feature amount calculator 102 calculates edge information, which is a directional feature amount included in the supplied low-band decomposition image data. In this embodiment, information on the size of the edge is calculated. To be specific, the information is calculated by using the tangent direction of the edge. The feature amount calculator 102 supplies the calculated information on the size of the edge to the high-band-level controller 105 and filtering processor 103 in the same hierarchy.

Moreover, the feature amount calculator 102 outputs the low-band decomposition image data to the filtering processor 103. The feature amount calculator 102 is equivalent to the "feature amount calculator" of the present invention.

The filtering processor 103 receives input of the low-band decomposition image data and the information on the size of the edge from the feature amount calculator 102. The filtering processor 103 uses a three-dimensional nonlinear anisotropic diffusion filter for the supplied low-band decomposition image data. The nonlinear anisotropic diffusion filter is a filter for emphasizing components that nonlinearly anisotropically diffuses. The edge components in the low-band decomposition image data anisotropically diffuses nonlinearly. Therefore, when the nonlinear anisotropic diffusion filter is used for the low-band decomposition image data, the luminance of the edge components is increased and non-edge components are reduced. Thus, by using the nonlinear anisotropic diffusion filter, the filtering processor 103 emphasizes the edge components included in the low-band decomposition image data to generate low-band decomposition image data with non-edge components smoothed. The filtering processor 103 is equivalent to the "filtering processor" of the present invention.

The detection of the edge information (the size of the edge in this embodiment) as a directional feature amount calculated by the feature amount calculator 102 and the filtering process with the nonlinear anisotropic diffusion filter by the filtering processor 103 will be described specifically. In this embodiment, the detection of the directional feature amount and the filtering process with the nonlinear anisotropic diffusion filter are achieved by obtaining eigenvalues and eigenvectors of a structure tensor of the low-band decomposition image data. The eigenvalues and eigenvectors of the structure tensor represent the direction of the edge, namely, the size of the edge of the low-band decomposition image data, respectively. In particular, a first eigenvalue and an eigenvector corresponding thereto represent the feature of low-band decomposition image data that has planar association both spatially and temporally. In the following description, the process shall be executed on low-band decomposition image data I, and the low-band decomposition image data I will be simply referred to as the "image I."

The structure tensor including the temporal direction of pixels in the image I is defined as shown below.

$$S = J_\rho(\nabla I) \quad \text{(Expression 1)}$$

$$= G_\rho * \begin{pmatrix} I_x^2 & I_xI_y & I_xI_t \\ I_xI_y & I_y^2 & I_yI_t \\ I_xI_t & I_yI_t & I_t^2 \end{pmatrix}$$

$$= \begin{pmatrix} s_{11} & s_{12} & s_{13} \\ s_{12} & s_{22} & s_{23} \\ s_{13} & s_{23} & s_{33} \end{pmatrix}$$

$$= R \begin{pmatrix} \lambda_{S1} & 0 & 0 \\ 0 & \lambda_{S2} & 0 \\ 0 & 0 & \lambda_{S3} \end{pmatrix} R^T$$

Herein, $I_x$ denotes spatial derivative in the x-direction of the image I, $I_y$ denotes spatial derivative in the y-direction of the image I, $I_t$ denotes temporal derivative in the t-direction (the temporal direction) of the image I, $G_\rho$ denotes a Gaussian function, and an operator "*" represents convolution. Moreover, $\lambda_{S1}$, $\lambda_{S2}$ and $\lambda_{S3}$ shall be eigenvalues of a structure tensor S, and the magnitude relation of the absolute values thereof shall be expressed as $\lambda_{S1} \geq \lambda_{S2} \geq \lambda_{S3}$. In this case, $\lambda_{S1}$ represents the first eigenvalue. A method for calculating the spatial derivative $I_x$, the spatial derivative $I_y$ and the temporal derivative $I_t$ is not limited to the calculation method described above. For example, instead of calculating $I_x$, $I_y$ and $I_t$, it is possible to use a sobel filter or high-band decomposition image data in multiresolution decomposition.

In a case that each element s in the structure tensor S has been obtained, the eigenvalues $\lambda_{S1}$, $\lambda_{S2}$ and $\lambda_{S3}$ and eigenvectors R and $R^T$ can be calculated by a well-known method in linear algebra. That is to say, the eigenvalues $\lambda_{S1}$, $\lambda_{S2}$ and $\lambda_{S3}$ of a 3×3 matrix in Expression 1 can be calculated by substantially solving a cubic equation by the Cardano's method, for example. Since the structure tensor S is a real symmetric matrix, the eigenvalues $\lambda_{S1}$, $\lambda_{S2}$ and $\lambda_{S3}$ are real numbers, and the eigenvectors R and $R^T$ are real vectors. The eigenvectors R and $R^T$ are orthogonal to each other. The eigenvalues $\lambda_{S1}$, $\lambda_{S2}$ and $\lambda_{S3}$ of the structure tensor S represent the size of the edge, and the eigenvectors R and $R^T$ represent the direction of the edge (the tangent direction of the edge).

In this embodiment, filtering based on the directional feature is expressed by a nonlinear diffusion equation (a partial differential equation) shown in the following expression.

$$\frac{\partial I}{\partial w} = div[D \nabla I] \quad \text{(Expression 2)}$$

Herein, I denotes a pixel level (a luminance value) of the image I, $\nabla I$ denotes a gradient vector thereof, and w denotes a temporal dimension in a physical diffusion equation. In other words, w denotes time relating to the process and, in actual process, denotes the number of processes in this diffusion equation. Moreover, D denotes a diffusion tensor, which is expressed by the following expression.

$$D = \begin{pmatrix} d_{11} & d_{12} & d_{13} \\ d_{12} & d_{22} & d_{23} \\ d_{13} & d_{23} & d_{33} \end{pmatrix} = R \begin{pmatrix} \lambda_{D1} & 0 & 0 \\ 0 & \lambda_{D2} & 0 \\ 0 & 0 & \lambda_{D3} \end{pmatrix} R^T \quad \text{(Expression 3)}$$

Herein, R is expressed by the following expression 4.

$$R = (\omega_1 \omega_2 \omega_3) \quad \text{(Expression 4)}$$

Herein, $\omega_1$, $\omega_2$, $\omega_3$ denote eigenvectors of the diffusion tensor D, and $\lambda_{D1}$, $\lambda_{D2}$, $\lambda_{D3}$ denote eigenvalues of the diffusion tensor D. Then, $\omega_1$ in $R=(\omega_1, \omega_2, \omega_3)$ represents the normal direction of the edge.

The eigenvalue $\lambda_{D1}$ of the diffusion tensor D represents the intensity of diffusion in a direction represented by the eigenvector $\omega_1$.

Similarly, the eigenvalue $\lambda_{D2}$ represents the intensity of diffusion in a direction represented by the eigenvector $\omega_2$, and the eigenvalue $\lambda_{D3}$ represents the intensity of diffusion in a direction represented by the eigenvector $\omega_3$. By controlling the values of the eigenvalues $\lambda_{D1}$, $\lambda_{D2}$ and $\lambda_{D3}$ for each pixel, the intensity of diffusion of the nonlinear anisotropic diffusion filter is controlled. The eigenvector R is synonymous with the filter direction of the nonlinear anisotropic diffusion filter. That is to say, by properly setting the eigenvector R, a desired filter direction of the nonlinear anisotropic diffusion filter is set.

Herein, the eigenvectors $\omega_1$, $\omega_2$ and $\omega_3$ of the diffusion tensor D are equal to unchanged eigenvectors of the structure tensor S of the pixels in the aforementioned image I, or the eigenvectors in a changed order. Moreover, the eigenvalues $\lambda_{D1}$, $\lambda_{D2}$ and $\lambda_{D3}$ of the diffusion tensor D depend on the size of the edge calculated from the eigenvalues $\lambda_{S1}$, $\lambda_{S2}$ and $\lambda_{S3}$ of the structure tensor S described above.

The edge information is expressed by Expression 5 shown below by using the eigenvalue $\lambda_{S1}$ of the first eigenvalue and the eigenvalue $\lambda_{S3}$ of the third eigenvalue. That is to say, the edge information is a value represented by using the size of the edge among the feature amount.

$$\text{edge} = 1 - \exp\left(-\frac{(\lambda_{S1} - \lambda_{S3})^2}{k^2}\right) \quad \text{(Expression 5)}$$

Herein, the edge has "magnitude" and "direction." The "magnitude" is such a parameter that becomes a "small" edge when change in intensity of an image is gentle while becomes a "large" edge when change in intensity of an image is steep.

The edge information is a parameter calculated by normalizing the size of the edge into a range from 0 to 1. The edge information represents that a component is closer to an edge component as the value of the edge information is closer to 1, whereas a component is closer to a non-edge component as the value of the edge information is closer to 0. A parameter k is a parameter showing the degree of extraction of edge components. That is to say, when the parameter k is decreased, edge components are extracted more easily.

Furthermore, the eigenvalues $\lambda_{D1}$, $\lambda_{D2}$ and $\lambda_{D3}$ of the diffusion tensor D are calculated by using the edge information. The eigenvalues $\lambda_{D1}$, $\lambda_{D2}$ and $\lambda_{D3}$ are expressed by Expressions 6, 7 and 8 shown below, respectively.

$$\lambda_{D1} = \beta_1(1-\text{edge}) + \beta_2 \cdot \text{edge} \quad \text{(Expression 6)}$$

$$\lambda_{D2} = \beta_3(1-\text{edge}) + \beta_4 \cdot \text{edge} \quad \text{(Expression 7)}$$

$$\lambda_{D3} = \beta_5(1-\text{edge}) + \beta_6 \cdot \text{edge} \quad \text{(Expression 8)}$$

In Expressions 6, 7 and 8, $\beta(1-\text{edge})$ represents a non-edge component while $\beta \cdot \text{edge}$ represents an edge component. The eigenvalues $\lambda_{D1}$, $\lambda_{D2}$ and $\lambda_{D3}$ represent the intensity of diffusion as described above. It is necessary to cause the non-edge component including speckle and noise as a reduction target not to have a directionality. That is to say, the non-edge component needs to be diffused without depending on a direction. For this, $\beta_1 = \beta_3 = \beta_5 > 0$ is set.

On the other hand, the directionality of an edge component as an emphasis target needs to be more emphasized. That is to say, it is necessary to sharpen the vertical direction of the edge component (the direction indicated by the eigenvector $\omega_1$ of the eigenvalue $\lambda_{D1}$), and diffuse the other directions (the direction indicated by the eigenvector $\omega_2$ of the eigenvalue $\lambda_{D2}$ and the direction indicated by the eigenvector $\omega_3$ of the eigenvalue $\lambda_{D3}$). Therefore, $\beta_2$ is set to a value approximate to 0, while $\beta_4$ and $\beta_6$ are set to predetermined values larger than $\beta_2$.

Accordingly, it is possible to calculate the eigenvalues $\lambda_{D1}$, $\lambda_{D2}$ and $\lambda_{D3}$ and the eigenvectors $\omega_1$, $\omega_2$ and $\omega_3$ of the diffusion tensor D.

Therefore, it is possible to calculate each element d of the diffusion tensor D in Expression 3, and obtain Expression 2 representing a nonlinear anisotropic diffusion filter (a diffusion equation).

Furthermore, calculation of this obtained nonlinear anisotropic diffusion filter (Expression 2) is performed by a numerical analysis of a partial differential equation. That is to say, from the respective pixel levels (pixel luminance values) at a certain point and points around the certain point as well as the respective element values of the diffusion tensor D at time w, a new pixel level at the certain point at time $w + \Delta w$ is obtained, and then the time $w + \Delta w$ is assumed as new time w. This calculation is repeatedly performed a predetermined number of times.

Figure 5B:
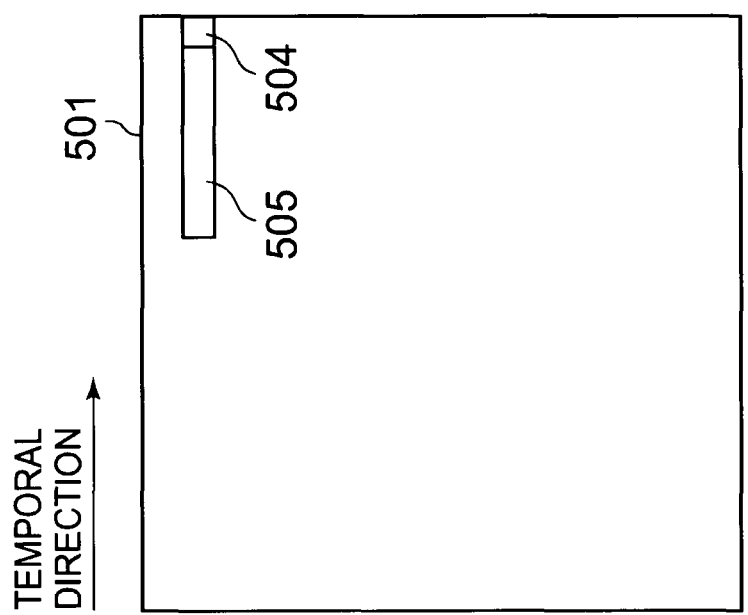
FIG. 5B is a view for explaining numerical differentiation in the temporal direction.
Figure 5A:
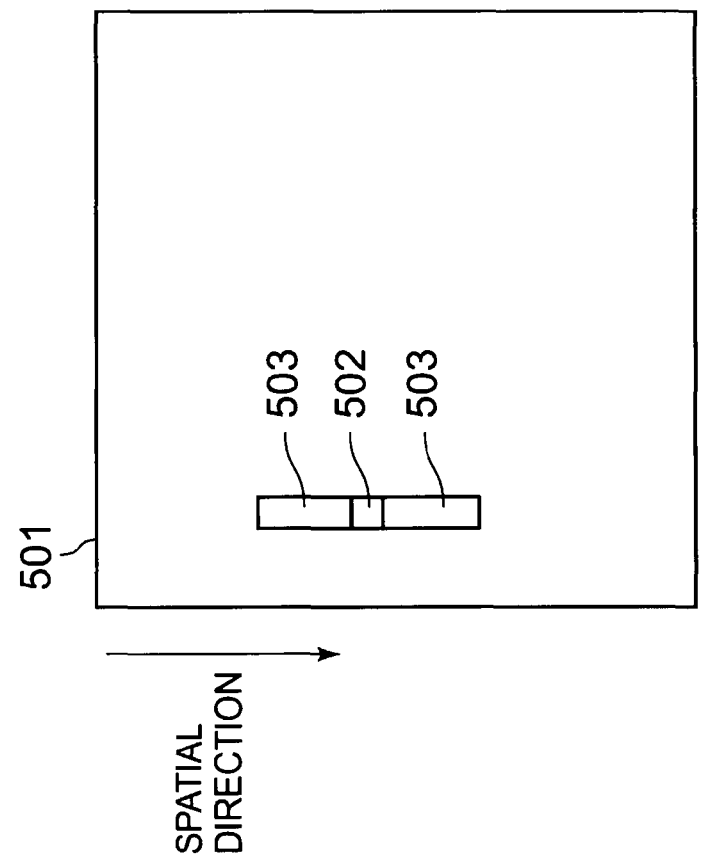
FIG. 5A is a view for explaining numerical differentiation in the spatial direction.

The numerical calculation method of Expression 2 will be described. Firstly, a method of numerical differentiation in the temporal direction will be described. FIG. 5A is a view for describing numerical differentiation in the spatial direction. FIG. 5B is a view for describing the numerical differentiation in the temporal direction.

Data 501 in FIGS. 5A and 5B has two coordinates of one-dimensional spatial coordinate and temporal coordinate. In FIG. 5A, the calculation of numerical differentiation and filtering in the spatial direction is performed with data 502 of a present position as the processing center by using data 503 of a predetermined number of near pixels on both the plus and minus sides of the processing center.

Taking one time of numerical differentiation for an example, when one near pixel on each of the plus and minus sides is used, the approximate of first-order numerical differentiation is expressed by Expression 9 shown below. This is called a three-point formula.

$$\frac{\partial I_i}{\partial x} \approx \frac{I_{i+1} - I_{i-1}}{2} \quad \text{(Expression 9)}$$

On the other hand, in FIG. 5B, numerical differentiation and filtering in the temporal direction are performed with present data 504 as the processing center. In FIG. 5B, a future time cannot be used for the processing. For example, in the case of setting the processing center to the past and using the same coefficient as in the spatial direction in the calculation equation, the processing result is temporally delayed from the present frame, and it is impossible to avoid a time phase delay. Therefore, numerical differentiation and filtering in the temporal direction need to be performed, with the present data 504 as the processing center, by using the present data 504 and past data 505 of a predetermined number of pixels.

When a function f(x) is continuous in an interval $[x_i, x_i + h]$, the following expression is obtained.

$$f'(x_i) = \frac{f(x_{i+1}) - f(x_i)}{h} - \frac{1}{h}\left\{\begin{array}{l} \frac{h^2}{2!} f''(x_i) + \\ \frac{h^3}{3!} f'''(x_i) + \ldots \end{array}\right\} \quad \text{(Expression 10)}$$

$R_{n+1}$ is a term that becomes a truncation error in numerical calculation. When $|h|$ is sufficiently small, $R_{n+1} = 0$ is obtained.

From the expression 10, the following expressions are obtained.

$$f(x_{i-1}) = f(x_i) - hf'(x_i) + \frac{h^2}{2!} f''(x_i) - \frac{h^3}{3!} f^{(3)}(x_i) + \ldots \quad \text{(Expression 11)}$$

$$f(x_{i-2}) = f(x_i) - 2hf'(x_i) + \frac{4h^2}{2!} f''(x_i) - \frac{8h^3}{3!} f^{(3)}(x_i) + \ldots \quad \text{(Expression 12)}$$

Then, the following expression is obtained from Expressions 11 and 12.

$$f'(x_i) = \frac{\begin{array}{c} 3f(x_i) - \\ 4f(x_{i-1}) + \\ f(x_{i-2}) \end{array}}{2h} - \left\{\frac{4h^3}{3!} f^{(3)}(x_i) + \ldots\right\} \quad \text{(Expression 13)}$$

When the value in the parentheses $\{\ \}$ of Expression 13 is considered as an error and omitted, the following expression is obtained.

$$f'(x_i) \approx \frac{3f(x_i) - 4f(x_{i-1}) + f(x_{i-2})}{2h} \quad \text{(Expression 14)}$$

As expressed by the expression 14, it is possible to obtain the approximate of the first-order numerical differentiation in the temporal direction, by using data of pixels of two frames of present data and past data. By using Expression 14, it is possible to perform calculation by the numerical calculation method of Expression 2.

To be specific, Expression 2 can be expressed as in the Expression 15 shown below.

$$\frac{\partial I}{\partial w} = div[D\nabla I] \quad \text{(Expression 15)}$$

$$= div\left[\begin{pmatrix} d_{11} & d_{12} & d_{13} \\ d_{12} & d_{22} & d_{23} \\ d_{13} & d_{23} & d_{33} \end{pmatrix}\left(\frac{\partial I}{\partial x} \quad \frac{\partial I}{\partial y} \quad \frac{\partial I}{\partial t}\right)^T\right]$$

$$= \frac{\partial}{\partial x}\left(d_{11}\frac{\partial I}{\partial x}\right) + \frac{\partial}{\partial x}\left(d_{12}\frac{\partial I}{\partial y}\right) + \frac{\partial}{\partial x}\left(d_{13}\frac{\partial I}{\partial t}\right) +$$

$$\frac{\partial}{\partial y}\left(d_{12}\frac{\partial I}{\partial x}\right) + \frac{\partial}{\partial y}\left(d_{22}\frac{\partial I}{\partial y}\right) + \frac{\partial}{\partial y}\left(d_{23}\frac{\partial I}{\partial t}\right) +$$

$$\frac{\partial}{\partial t}\left(d_{13}\frac{\partial I}{\partial x}\right) + \frac{\partial}{\partial t}\left(d_{23}\frac{\partial I}{\partial y}\right) + \frac{\partial}{\partial z}\left(d_{23}\frac{\partial I}{\partial t}\right)$$

For calculating partial differentiation of each term of Expression 15, the approximate values of Expressions 9 and 14 described above are used.

The aforementioned processing procedure of the nonlinear anisotropic diffusion filter will be described with reference to FIG. 6.

FIG. 6 is a flow chart showing the processing procedure of a filtering process of the nonlinear anisotropic diffusion filter in the third-order hierarchy. Although a filtering process in the third-order hierarchy will be described below as an example, the same processing is performed in the filtering process in the first-order or second-order hierarchy.

Step S001: The multiresolution decomposition part 101c receives, from the multiresolution decomposition part 101b, input of data to be filtered.

Step S002: The multiresolution decomposition part 101c performs differentiation of the inputted data in the respective coordinate axis directions ($I_x$, $I_y$, $I_t$) to generate low-band decomposition image data and high-band decomposition image data.

Step S003: The feature amount calculator 102c calculates the respective elements of the structure tensor S of the low-band decomposition image data inputted from the multiresolution decomposition part 101c. This calculation includes calculation of the Gaussian function $G_\rho$ before the calculation of the structure tensor S.

Step S004: The feature amount calculator 102c calculates the eigenvalues $\lambda_{s1}$, $\lambda_{s2}$ and $\lambda_{s3}$ and the eigenvectors $\omega_1$, $\omega_2$ and $\omega_3$ from the structure tensor S.

Step S005: The feature amount calculator 102c obtains the size of the edge from the eigenvalues $\lambda_{s1}$, $\lambda_{s2}$ and $\lambda_{s3}$ of the structure tensor S and the direction of the edge from the eigenvectors $\omega_1$, $\omega_2$ and $\omega_3$.

Step S006: The feature amount calculator 102c outputs the obtained size of the edge to the high-band-level controller 105c in the same hierarchy.

Step S007: The filtering processor 103c calculates the intensity of diffusion based on the size of the edge obtained by the feature amount calculator 102c, and furthermore calculates, from the obtained intensity of the diffusion and the eigenvectors $\omega_1$, $\omega_2$ and $\omega_3$ of the structure tensor S, the respective coefficients used in the numerical analysis of the diffusion equation (Expression 2) of the nonlinear anisotropic diffusion filter.

Step S008: The filtering processor 103c performs numerical analytical calculation of the diffusion equation.

Step S009: The filtering processor 103c determines whether the numerical analytical calculation of the diffusion equation has been performed a predetermined number of times. In a case that the calculation has not been performed the predetermined number of times, the process returns to step S008. In a case that the calculation has been performed the predetermined number of times, the process advances to step S010.

Step S010: The filtering processor 103c outputs the low-band decomposition image data after the filtering process by the nonlinear anisotropic diffusion filter, to the multiresolution composition part 104c in the same hierarchy.

The high-band-level controller 105 receives input of eight high-band decomposition image data from the multiresolution decomposition part 101 in the same hierarchy. Moreover, the high-band-level controller 105 receives input of the size of the edge from the feature amount calculator 102. The high-band-level controller 105 executes, on the high-band decomposition image data, a process of emphasizing the edge portion by using information of the edge (the size of the edge). In this embodiment, the high-band-level controller 105 calculates, for each pixel, the product of the size of the edge calculated from the eigenvalues of the diffusion tensor D and the respective high-band decomposition image data. Moreover, the high-band-level controller 105 multiplies the product by a control coefficient of each of the high-band decomposition image data. By thus calculating the product of the size of the edge and the high-band decomposition image data, it is possible to emphasize the edge portion while inhibiting a portion other than the edge in this data.

Another method for processing the high-band decomposition image data using the size of the edge (the edge information) is a method of multiplying a region other than the edge by a control coefficient of each high-band image. By performing such a process, it is possible to emphasize the edge portion in the high-band decomposition image data. The high-band-level controller 105 outputs the high-band decomposition image data after the aforementioned process of emphasizing the edge portion, to the multiresolution composition part 104 in the same hierarchy. This high-band-level controller 105 is equivalent to the "high-band-level controller" of the present invention.

The multiresolution composition part 104 receives input of one low-band decomposition image data from the filtering processor 103.

Further, the multiresolution composition part 104 receives input of seven high-band decomposition image data from the high-band-level controller 105. The multiresolution composition part 104 composes the one low-band decomposition image data and seven high-band decomposition image data having been inputted to generate one composite image. When generating a composite image, the multiresolution composition part 104 performs inverse wavelet transform based on the one low-band decomposition image data and the seven high-band decomposition image data. In this generated composite image, the number of samples per coordinate axis is twice that in the image inputted from the filtering processor 103. The multiresolution composition part 104 in the second-order or higher-order hierarchy (the multiresolution composition part 104b or 104c in this embodiment) outputs the formed image to the feature amount calculator 102 in a next lower hierarchy.

Further, the multiresolution composition part 104 in the first-order hierarchy (the multiresolution composition part 104a in this embodiment) outputs the formed image to the image generator 004.

This multiresolution composition part 104 is equivalent to the "multiresolution composition part" of the present invention.

With reference to FIG. 7, the flow of a general operation of the ultrasound diagnosis apparatus according to this embodiment will be described. FIG. 7 is a flow chart of the general operation of the ultrasound diagnosis apparatus according to this embodiment. A B-mode image will be taken for an example below again.

Step S101: The transceiver 002 transmits ultrasound waves to a subject via the ultrasound probe 001, and receives echo signals based on ultrasound echoes reflected by the subject.

Step S102: The signal processor 003 executes signal processing such as logarithmic compression and envelope detection on the echo signals inputted from the transceiver 002.

Step S103: The speckle/noise reduction processor 100 stores B-mode data inputted from the signal processor 003 into the frame accumulator 106 for each frame.

Step S104: Based on B-mode data of a predetermined number of frames back from latest B-mode data stored in the frame accumulator 106, the speckle/noise reduction processor 100 performs multiresolution decomposition, feature amount calculation, filtering process, high-band-level control, and multiresolution composition to execute the speckle/noise reduction process on the latest B-mode data.

Step S105: The image generator 004 executes, on the B-mode data inputted from the speckle/noise reduction processor 100 after the speckle/noise reduction process, coordinate axis conversion or the like to generate an ultrasound image of the B-mode data.

Step S106: The display controller 005 causes the display 007 to display the ultrasound image inputted from the image generator 004.

Step S107: The integrated controller 009 determines whether the examination has finished. In a case that the examination has not finished, the process returns to step S101. In a case that the examination has finished, the operation of the ultrasound diagnosis apparatus is stopped.

The above description has been made by using a two-dimensional tomographic image as a target of the speckle/noise reduction process. As a target of the speckle/noise reduction process, it is also possible to use a three-dimensional tomographic image such as three-dimensional volume data. The speckle/noise reduction process on a three-dimensional tomographic image can be executed by adding one dimension to the aforementioned process. To be specific, in the calculation of the size of the edge and the calculation in the filtering process, one row and one column can be added to the matrix.

The speckle/noise reduction processor 100 is placed after the signal processor 003. The speckle/noise reduction processor 100 may be placed after the image generator 004. In a case that the speckle/noise reduction processor 100 is placed after the image generator 004, the speckle/noise reduction process is executed on an ultrasound image on which the coordinate axis conversion has been executed. In this case, the ultrasound probe 001, the transceiver 002, the signal processor 003, and the image generator 004 are equivalent to the "image generator" of the present invention, and the display controller 005 is equivalent to the "display controller" of the present invention.

As described above, the ultrasound diagnosis apparatus according to this embodiment performs multiresolution decomposition in the spatial direction and the temporal direction of raw data in each mode such as B-mode or Doppler mode to calculate a directional feature amount. By using a filter utilizing the directional feature amount, change in noise and speckle in the spatial direction and the temporal direction is reduced. Consequently, it is possible to generate such an image that is smooth not only in the spatial direction but also in the temporal direction and has an emphasized tissue part.

Further, the ultrasound diagnosis apparatus according to this embodiment is configured to calculate, for numerical differentiation in the temporal direction, by using data of plural frames including present and past frames, by an equation and coefficient different from those for the spatial direction. Consequently, a filtering process without a time phase delay is allowed.

Further, in this embodiment, an image with the more emphasized edge is generated by using the high-band-level controller 105 to execute the process on high-band decomposition image data and emphasize an edge portion of the high-band decomposition image data.

However, it is also possible to generate a composite image in the multiresolution composition part 104 by using high-band decomposition image data as it is, without using the high-band-level controller 105 and without executing the process on the high-band decomposition image data. In this case, though the degree of emphasis of a tissue portion becomes weaker than in the case of using the high-band-level controller 105, it becomes possible to generate an image that is smooth in the temporal direction.

The multiresolution decomposition part 101, the feature amount calculator 102, the filtering processor 103, the multiresolution composition part 104, and the high-band-level controller 105 may be placed for each hierarchy (for each order from the first-order to the $n^{th}$-order in FIG. 2). The process in each hierarchy (each order) may be sequentially performed by one set of multiresolution decomposition part 101, feature amount calculator 102, filtering processor 103, multiresolution composition part 104 and high-band-level controller 105.

Second Embodiment

An ultrasound diagnosis apparatus according to a second embodiment of the present invention will be described below. The ultrasound diagnosis apparatus according to this embodiment is different in configuration from the first embodiment in that B-mode data after the speckle/noise reduction process is used to execute the speckle/noise reduction process on a next frame. The configuration of the ultrasound diagnosis apparatus according to this embodiment will be shown by the block diagram of FIG. 1. In the following description, function parts denoted by the same reference numerals as in the first embodiment have the same functions as far as there is no specific description.

Figure 8:
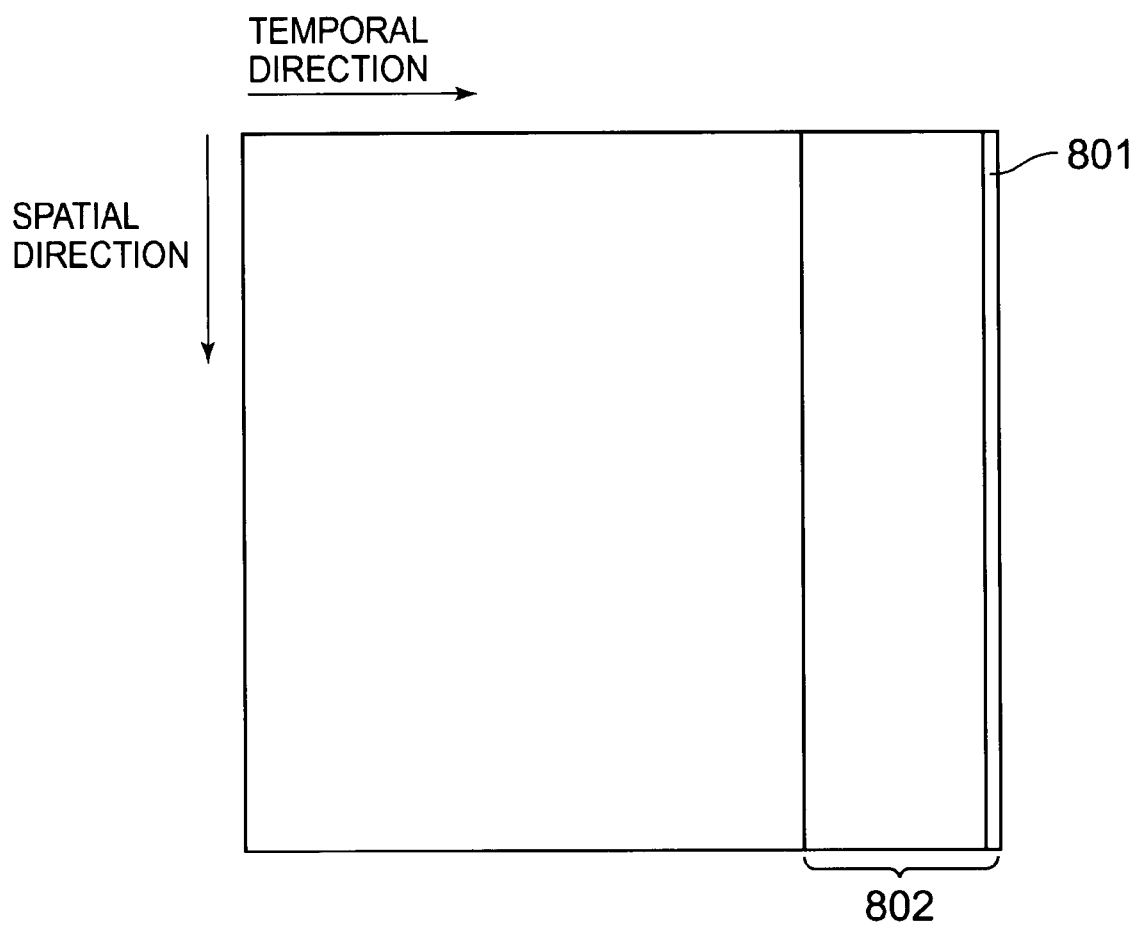
FIG. 8 is a view for explaining accumulation of B-mode data and a speckle/noise reduction process using the accumulated B-mode data in a second embodiment.

FIG. 8 is a view for describing accumulation of B-mode data and a process using the accumulated B-mode data. In order to facilitate the description, FIG. 8 shows two dimensions of the spatial axis and temporal axis.

The frame accumulator 106 stores B-mode data inputted from the signal processor 003 sequentially with time. The latest B-mode data is B-mode data 801. The speckle/noise reduction processor 100 performs the speckle/noise reduction process on the B-mode data 801 by using set B-mode data 300. The set B-mode data 300 is the set of B-mode data of a predetermined number of frames including the B-mode data 801 stored in the frame accumulator 106.

Then, the frame accumulator 106 deletes the unprocessed B-mode data 801, and stores the B-mode data 801 having been processed (referred to as the processed B-mode data 801 hereinafter) as B-mode data of the latest frame. After that, when B-mode data of the next frame (referred to as B-mode data 802) is inputted from the signal processor 003, the B-mode data 802 is stored as the latest frame into the frame accumulator 106. Then, the speckle/noise reduction processor 100 executes the speckle/noise reduction process on the B-mode data 802, and the frame accumulator 106 stores the processed B-mode data 802. By repeating the process as described above, the processing results of the past B-mode data are accumulated in the temporal direction into the frame accumulator 106, and it is possible to perform the speckle/noise reduction process of the latest B-mode data by using the accumulated processed B-mode data. The frame accumulator 106 is equivalent to the "data accumulator" in the present invention.

Thus, the ultrasound diagnosis apparatus according to this embodiment is configured to execute the speckle/noise reduction process on the latest B-mode data by using the past B-mode data on which the speckle/noise reduction process has been executed.

Consequently, since it is possible to use smooth B-mode data having already been processed in the speckle/noise reduction process in the temporal direction, it becomes possible to more efficiently reduce change in speckle/noise in the temporal direction and perform a process without a time phase delay.

(Modification 1)

Next, another example of the ultrasound diagnosis apparatus according to the present invention will be described. In this modification, unprocessed B-mode data are accumulated. At the time of execution of the speckle/noise reduction process, the latest unprocessed frame is outputted to the frame accumulator 106.

FIG. 9 is a view for describing accumulation of B-mode data and the process using the accumulated B-mode data in this modification.

FIG. 9 is expressed in two-dimensions of the spatial axis and the temporal axis.

The ultrasound diagnosis apparatus of this modification has a configuration that an unprocessed frame accumulator 107 shown by a dotted line is added to the ultrasound diagnosis apparatus according to the second embodiment.

The unprocessed frame accumulator 107 has a storing medium such as a memory and a hard disk.

The unprocessed frame accumulator 107 stores B-mode data inputted from the signal processor 003 sequentially with time. The unprocessed frame accumulator 107 may store B-mode data of all the frames, or may store B-mode data of a predetermined number of frames.

In the configuration to store B-mode data of a predetermined number of frames, when new unprocessed B-mode data 901 is inputted, the oldest unprocessed B-mode data is deleted.

The frame accumulator 106 requests input of the B-mode data 901 before the speckle/noise reduction process, to the unprocessed frame accumulator 107. In response to the input request, the unprocessed frame accumulator 107 inputs the latest unprocessed B-mode data 901 into the frame accumulator 106.

The frame accumulator 106 stores B-mode data 902 after the speckle/noise reduction process of frames of one less than a predetermined number. The frame accumulator 106 outputs, to the multiresolution decomposition part 101, the unprocessed B-mode data 901 copied from the unprocessed frame accumulator 107 and the stored processed B-mode data 902. Then, the frame accumulator 106 stores the processed B-mode data after the speckle/noise reduction process by the speckle/noise reduction processor 100. At this moment, the frame accumulator 106 deletes the oldest processed B-mode data.

With such a configuration, it is also possible to more efficiently reduce change in speckle/noise in the temporal direction and perform a process without a time phase delay.

What is claimed is:

1. An ultrasound diagnosis apparatus, comprising:
an image generator configured to execute transmission and reception of ultrasound waves to chronologically generate ultrasound image data of plural frames;
a multiresolution decomposition part configured to hierarchically execute multiresolution decomposition on the ultrasound image data of plural frames to obtain first-order to $n^{th}$-order (n represents a natural number of 2 or more) low-band decomposition image data and first-order to $n^{th}$-order high-band decomposition image data;
a feature amount calculator configured to calculate a feature amount based on the obtained low-band decomposition image data;
a filtering processor configured to execute a filter operation on the calculated feature amount of ultrasound image data which becomes a filtering processing object based on a feature amount calculated by ultrasound image data of plural frames imaged at time prior to a time at which a frame of the ultrasound image data is imaged; and
a multiresolution composition part configured to execute multiresolution composition by using the low-band decomposition image data and the high-band decomposition image data to generate a composite image.

2. The ultrasound diagnosis apparatus according to claim 1, further comprising a data accumulator configured to store the ultrasound image data, wherein the filtering processor is configured to, as a filtering process on ultrasound image data of a $t^{th}$ frame among the plural frames, numerically analyze a diffusion equation by using pixel values of pixels at a same position in ultrasound image data of each of frames of a predetermined number of frames back from a $(t-1)^{th}$ frame stored in the data accumulator to calculate pixel values of respective pixels at the same position in ultrasound image data of the $t^{th}$ frame.

3. The ultrasound diagnosis apparatus according to claim 1, further comprising a data accumulator configured to store the low-band decomposition image data, wherein the filtering processor is configured to, as a filtering process on ultrasound image data of a $t^{th}$ frame, numerically analyze a diffusion equation by using pixel values of pixels at a same position in low-band decomposition image data of each of frames of a predetermined number of frames back from a $(t-1)^{th}$ frame stored in the data accumulator to calculate pixel values of respective pixels at the same position in processed low-band decomposition image data of the $t^{th}$ frame.

4. The ultrasound diagnosis apparatus according to claim 1, wherein:
the filtering processor is configured to use a filter expressed by a nonlinear diffusion equation; and
in the case of execution of numerical analysis of the nonlinear diffusion equation, $$\partial I_t / \partial x = \{I_{i+1} - I_{i-1}\}/2$$

is used as numerical differentiation in a spatial direction and $$\partial I_t / \partial t = \{3I_t - 4I_{t-1} - I_{t-2}\}/2$$

is used as numerical differentiation in a temporal direction, wherein $I_i$ represents a pixel value when x is i and $I_t$ represents a pixel value at time t.

5. The ultrasound diagnosis apparatus according to claim 1, wherein the feature amount calculator is configured to calculate a structure tensor of each pixel, calculate eigenvalues and eigenvectors by using the structure tensor, and calculate a feature amount by using the eigenvalues and the eigenvectors.

6. The ultrasound diagnosis apparatus according to claim 1, wherein the filtering processor is configured by a nonlinear anisotropic diffusion filter.

7. The ultrasound diagnosis apparatus according to claim 1, further comprising a high-band-level controller configured to execute a filtering process of emphasizing an edge on the high-band decomposition image data and output the processed high-band decomposition image data to the multiresolution composition part.

8. An ultrasound diagnosis apparatus, comprising:
- an image generator configured to execute transmission and reception of ultrasound waves to chronologically generate ultrasound image data of plural frames;
- a multiresolution decomposition part configured to hierarchically execute multiresolution decomposition on the ultrasound image data to obtain first-order to $n^{th}$-order (n represents a natural number of 2 or more) low-band decomposition image data and first-order to $n^{th}$-order high-band decomposition image data;
- a multiresolution composition part configured to perform multiresolution composition by using the low-band decomposition image data and the high-band decomposition image data to generate a composite image;
- a feature amount calculator configured to calculate a feature amount based on the obtained low-band decomposition image;
- a filtering processor configured to perform a filter operation on the calculated feature amount of ultrasound image data which becomes a filtering processing object based on a feature amount calculated by ultrasound image data of plural frames imaged at time prior to time in which a frame of the ultrasound image data is imaged; and
- a high-band-level controller configured to weight the first-order to $n^{th}$-order high-band decomposition image data obtained from the multiresolution decomposition part, by a feature amount of each corresponding order.

* * * * *